United States Patent [19]

Hogan

[11] 4,217,064
[45] Aug. 12, 1980

[54] LATCHING MECHANISM

[75] Inventor: William F. Hogan, Westville, N.J.

[73] Assignee: Spectrum X-Ray Corporation, Westville, N.J.

[21] Appl. No.: 920,345

[22] Filed: Jun. 29, 1978

[51] Int. Cl.² .................. F16C 11/00; F16D 1/12; F16D 3/00
[52] U.S. Cl. .................................. 403/33; 403/318; 403/324
[58] Field of Search ............. 403/33, 49, 316, 317, 403/322, 324, 325, 328; 292/169 R, 257, 37

[56] References Cited

U.S. PATENT DOCUMENTS

| | | | |
|---|---|---|---|
| 416,359 | 12/1889 | Cooley | 292/257 |
| 1,431,562 | 10/1922 | Bolles | 292/37 X |
| 1,605,717 | 11/1926 | Gregg | 292/37 X |
| 3,104,909 | 9/1963 | Walker | 403/322 X |
| 3,834,198 | 9/1974 | Wiczer | 292/169 X |
| 4,136,792 | 1/1979 | Wilson | 403/33 X |

FOREIGN PATENT DOCUMENTS 601637  7/1978  Switzerland ..................... 292/169

Primary Examiner—Wayne L. Shedd
Attorney, Agent, or Firm—Paul & Paul

[57] ABSTRACT

Several forms of latching mechanism are disclosed incorporating a pivotal cam and a spring-loaded plunger. In the preferred form, a lock pin is also included. The latching mechanism is particularly suited for latching interfitted members at least one of which is tubular. In one preferred form, the members are prevented from being interfitted by the lock pin which bars entry into the tubular member. The lock pin may be withdrawn only when the tubular member occupies a preselected orientation relative to a fixed frame member. When so oriented, the plunger's hose is received within a recess. This allows pivotal movement of the cam lever, and permits withdrawal of the lock pin. After the members have been interfitted, the lock pin is reinserted by pivotal movement of the cam lever. In its reinserted position, the lock pin enters aligned slots in the members, thereby locking the interfitted members together. Once the lock pin has been reinserted to lock the interfitted members together, the lock pin may not be withdrawn unless the members occupy a preselected orientation relative to the frame member.

4 Claims, 12 Drawing Figures

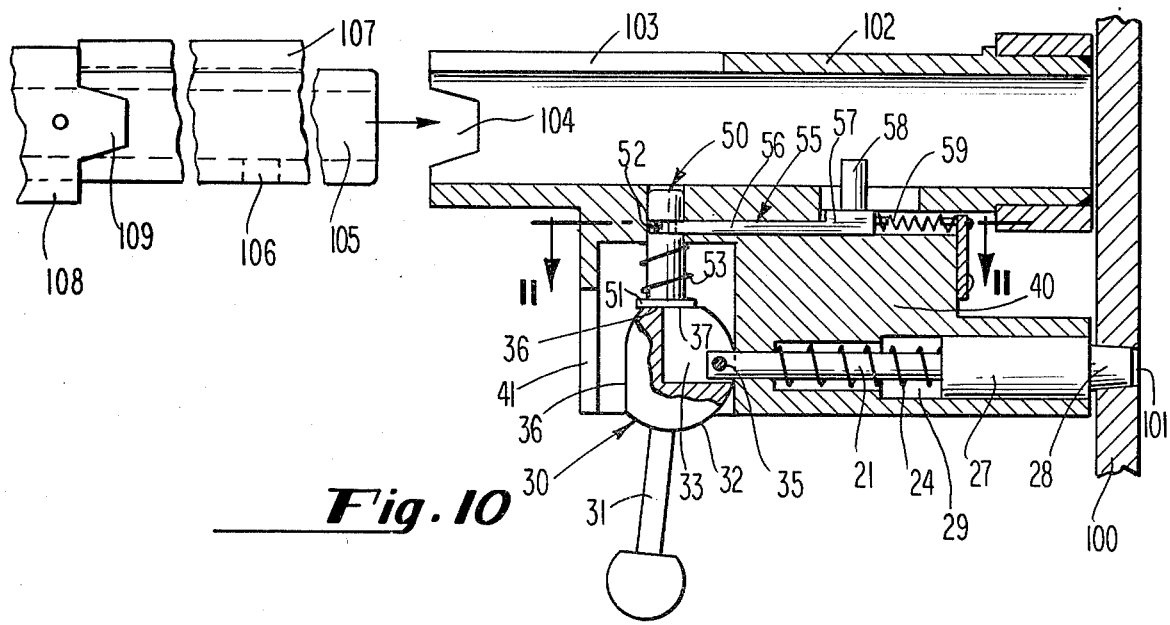
_Fig. 10_
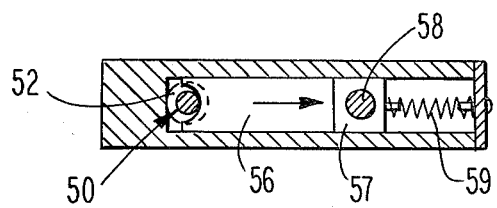
_Fig. 11_
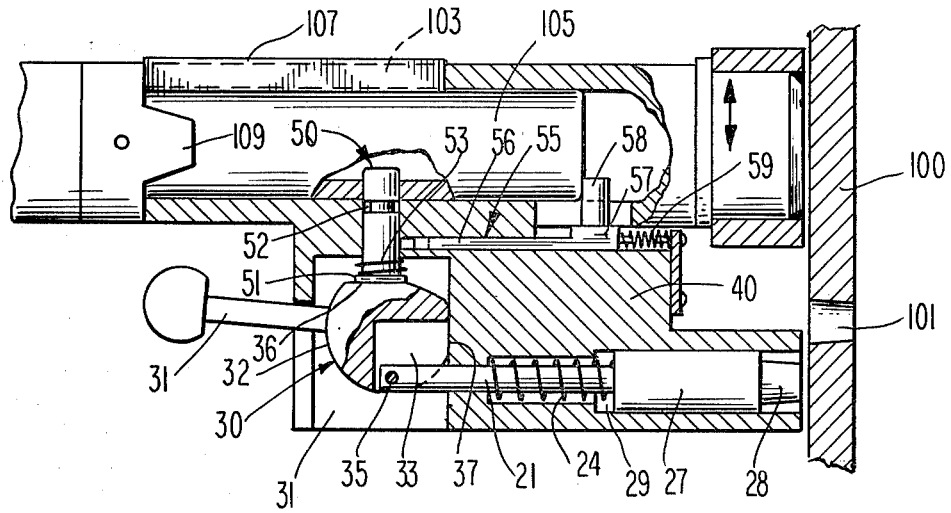
_Fig. 12_

LATCHING MECHANISM

BACKGROUND OF THE INVENTION

This invention relates to manually operable latching mechanisms which have wide applications but are particularly useful in X-ray equipments, particularly X-ray equipments of the type shown in my co-pending patent application Ser. No. 865,172, filed Dec. 28, 1977, now U.S. Pat. No. 4,158,777, issued June 19, 1979.

In X-ray examination of patients, it is undesirable to have the X-ray tube emit an X-ray beam in any direction other than toward the image amplifier. When, for any reason, the X-ray tube and image amplifier are mechanically disconnected, it is desirable, from a precautionary and safety point of view, that the X-ray tube be in such orientation that its beam is directed vertically upward as otherwise the beam may be projected in such horizontal or inclined direction as to expose persons in the room to possible X-ray radiation.

SUMMARY OF THE INVENTION

Several forms of latching mechanisms are disclosed.

In one form, the latching mechanism is adapted for indexing a pivotally rotatable housing, such as an X-ray image amplifier, to a selected angular position or orientation.

In another form, the latching mechanism is adapted for connecting, and quickly disconnecting, male and female connections, thereby to allow for rapid withdrawal of the X-ray image amplifier, as for example, from the heart region under emergency conditions.

In yet another form, the latching mechanism is adapted for latching and unlatching inter-fitted male and female connections, but only if the X-ray tube occupies a preselected safe orientation or angular position.

BRIEF DESCRIPTION OF THE DRAWING

FIG. 10 is a plan view looking down along the line 10—10 of FIG. 6 showing the latch pin in unlatched position.

FIG. 11 is a detailed view looking along the line 11—11 of FIG. 10.

FIG. 12 is a plan view similar to FIG. 10 but showing the latch pin in latched position.

DETAILED DESCRIPTION OF THE PREFERRED EMBODIMENTS

Figure 1:
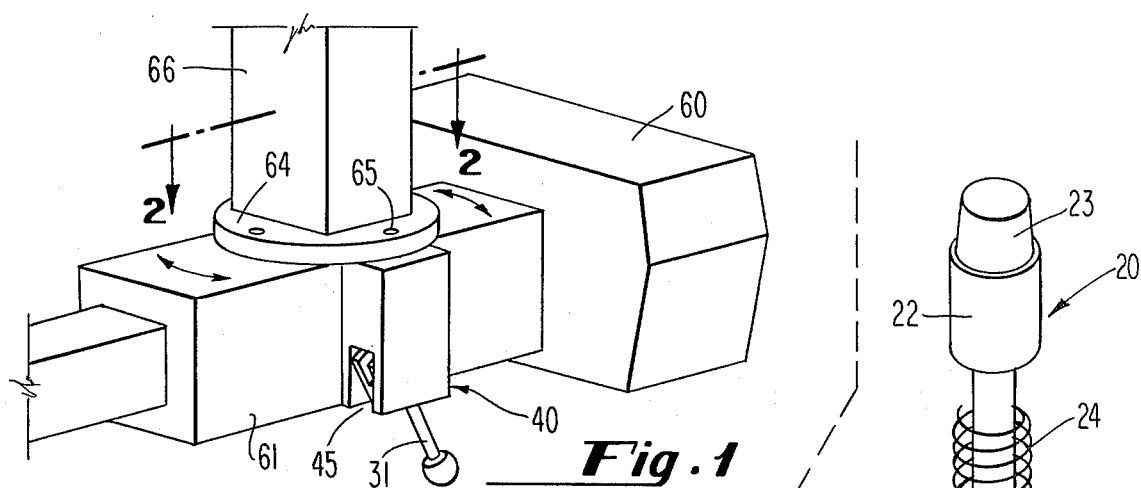
FIG. 1 is a perspective view of an X-ray image amplifier system suspended from a vertically disposed telescopic support assembly and pivotally indexed with respect to the vertical axis thereof and latched into selected indexing positions by one form of latching mechanism provided by the present invention.

The form of latching mechanism shown in FIGS. 2–5 will be described first. This mechanism is shown exploded in FIG. 5. As there seen, a plunger 20 has a shank 21 having at one end an enlarged head 22 having a nose portion 23. The other end of the shank is provided with a transverse hole 25 for receiving a pin 35 by means of which the plunger 20 is secured to an eccentric cam 30. Eccentric cam 30 has a generally circular surface portion 32 and a flat surface portion 36. It has a central slot 33 which receives the shank 21 of the plunger 20. Eccentrically positioned holes 34 in the cam receive the pin 35 which secures the plunger 20 to the cam.

Cam 30 is provided with a lever 31 for manual operation of the cam. The cam 30 and plunger 20 are installed in a body 40 having a cavity 45 which receives the cam 30 and a cavity 29 which receives the plunger 20. A compression spring 24 supported on shank 21 of the plunger 20 has one end thrusting against the base of the cavity 29 and the other end thrusting against the head of the plunger. This spring maintains the edge surface of cam 30 in contact with the walls of cavity 45.

Figure 3:
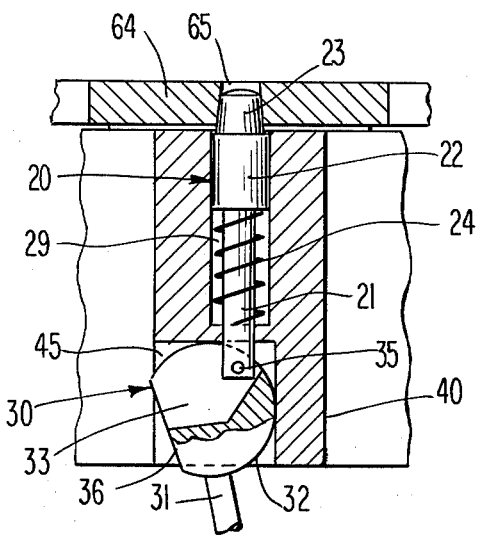
FIG. 3 is an elevational view, in section, looking along the line 3—3 of FIG. 2 showing the latch plunger in latched position.

In FIG. 3, the latch mechanism just described is shown in latched position. In this position, the nose 23 of the plunger 20 is in a recess or hole 65 provided in a plate 64. The compression spring 24 functions to maintain the plunger in the outward or latched position, and, as previously stated, keeps the edge surfaces of cam 30 tightly against the wall surfaces of the cavity 45. In the latched position, latch body 40 is prevented from being moved laterally relative to the plate 64.

An examination of FIG. 3 will show that when the mechanism is in the latched position, retraction of the nose from the detent requires a force which is not only sufficient to overcome the compressional resistance of spring 24 but also sufficient to pivot the eccentric cam 30 about a center axis which must shift laterally during rotation. This follows from the fact that pin 35 is constrained to be movable only along a straight line corresponding to a projection of the center axis of the plunger 20. Constraint of movement of pin 35 along this line results from the fact that the head 22 of the plunger is constrained within the plunger cavity 29. Thus, removal of the nose 23 of plunger 20 from the slot 65 in which it is shown in FIG. 3 requires application of a lateral force to the eccentric cam 30.

Figure 4:
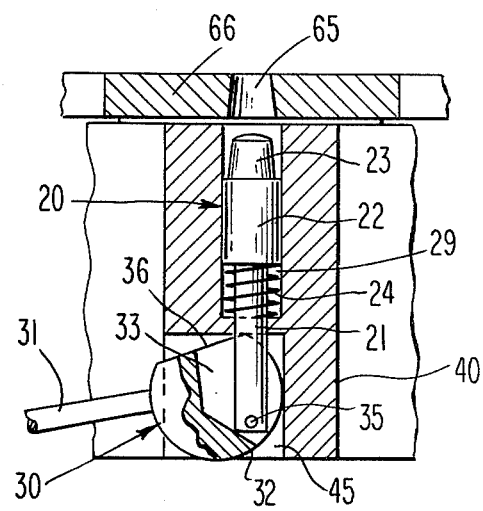
FIG. 4 is a view similar to FIG. 3 but showing the latch plunger in unlatched position.

FIG. 4 illustrates the mechanism in unlatched position. This position is obtained by pivoting cam lever 31 from the position shown in FIG. 3 to the position shown in FIG. 4. In FIG. 4, plunger 20 is in its retracted position, the compression spring 24 is unable to move the plunger outwardly because the force of spring 24 is insufficient to cause pivotal movement of the cam 30 about a center axis, which must shift laterally to the left as the cam rotates. Note, also that the point on the cam surface where flat 36 meets the curved surface 32 is bearing against the wall of cavity 45, and that this point must shift laterally if the plunger is to move outwardly.

Thus, the plunger is maintained in the retracted position.

Figure 8:
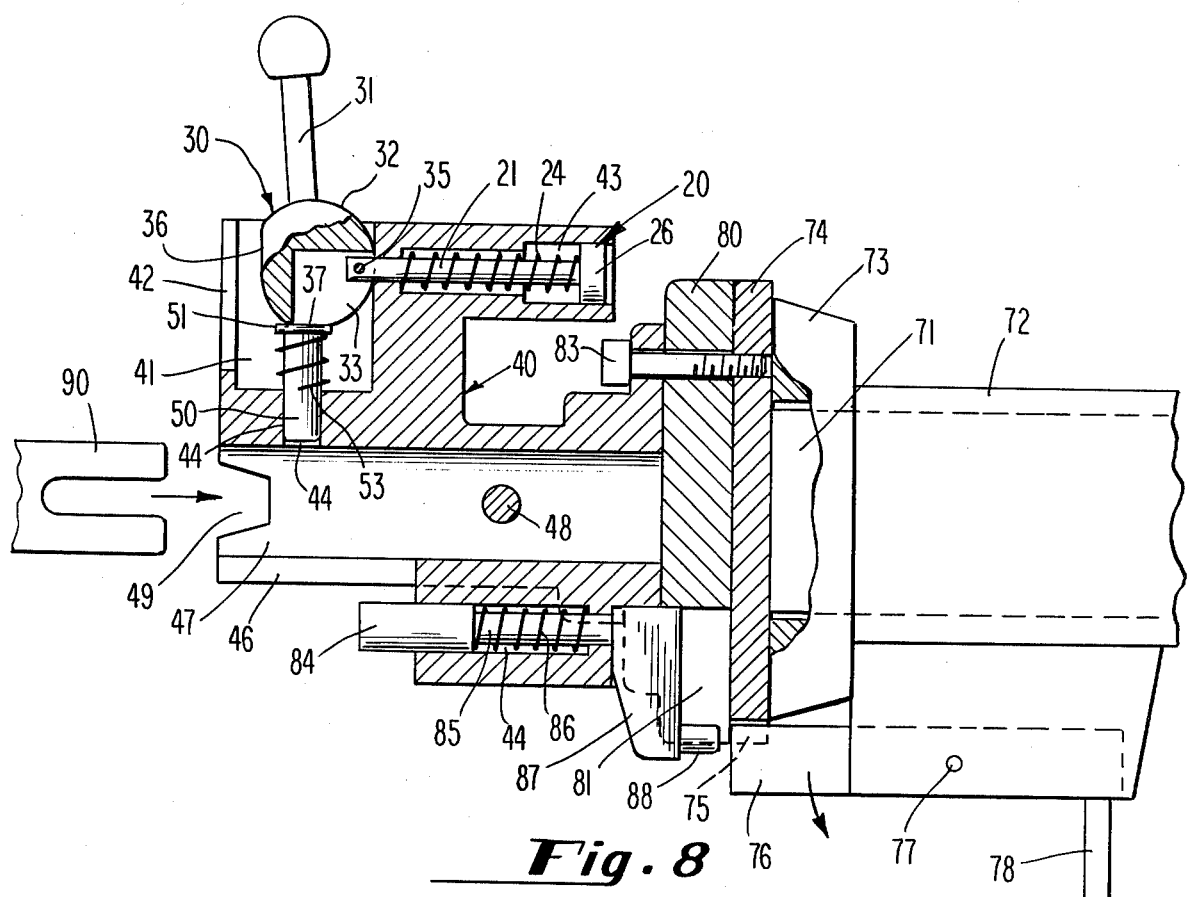
FIG. 8 is an elevational view looking along the lines 8—8 of FIG. 7 showing the latch pin in unlatched position.
Figure 9:
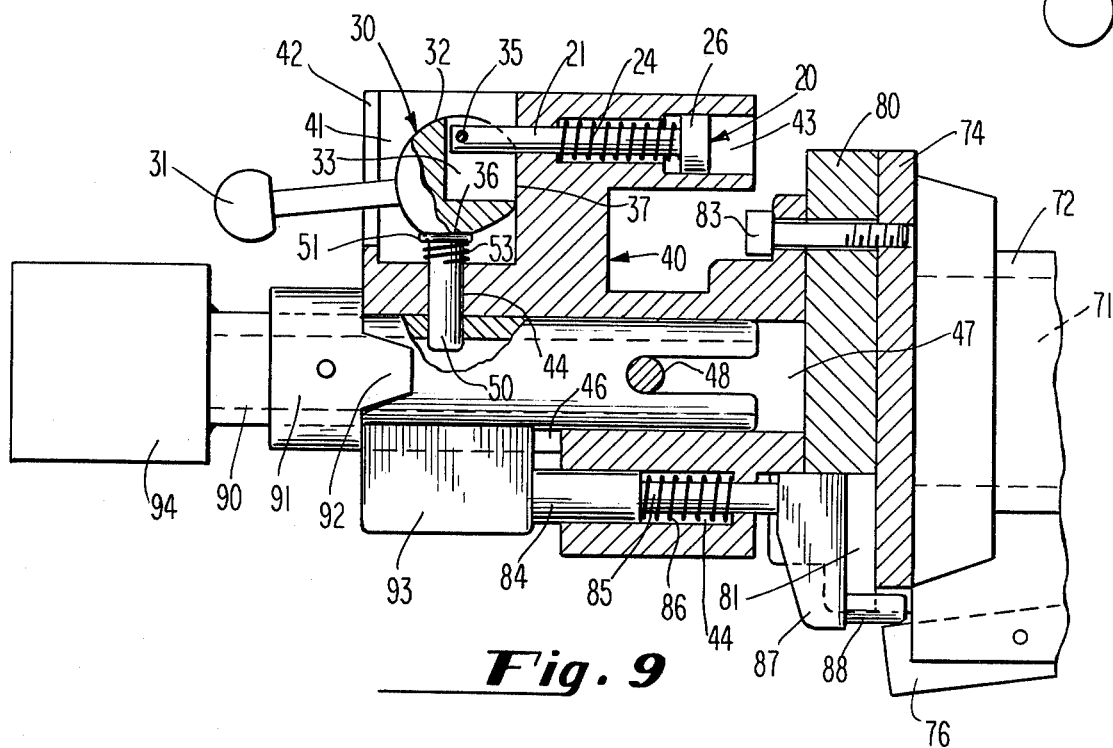
FIG. 9 im similar to FIG. 8 but shows the latch pin in latched position.

FIGS. 8 and 9 illustrate another form of latching mechanism of the present invention employed to connect and disconnect male and female members. In FIGS. 8 and 9, the male member is a cylindrical shaft 90 having a clevis at its forward end and adapted to be received within tubular female member 47. A clevis pin 48 is provided in female member 47.

In FIGS. 8-9, the cam surface has two flats 36 and 37. In FIG. 8, the lock pin 50 is shown in retracted position. A spring loaded plunger 20 holds curved surface 32 of the cam against the wall of the cavity 41.

A compression spring 53 biases the head 51 of lock pin 50 against the flat 37 of the cam 30. When the cylindrical shaft 90 is inserted into the tubular member 47 to a limit position determined by clevis pin 48, a hole in the wall of the shaft 90 comes into registry with hole 44 which holds the lock pin 50. Proper angular orientation of shaft 90 relative to tubular member 47 is obtained by a collar 91 pinned to shaft 90. Collar 91 has a wedge-shaped forward projection 92 which fits into a wedge-shaped recess 49 in the end of female member 47.

With shaft 90 inserted into female member 47, as just described, the lever 31 of the eccentric latching mechanism may now be pivoted counterclockwise from the position shown in FIG. 8 to the position shown in FIG. 9. When lever 35 is so pivoted, the pivot axis of the cam 30 shifts downwardly from a position substantially in line with the center axis of the plunger 20 to a position substantially below that of the axis of plunger 20. This movement is forced by eccentric pin 35 which moves laterally, toward the left as viewed in FIGS. 8 and 9, along the projected center axis of plunger 20. A previously indicated in connection with FIGS. 2-5, the movement of eccentric pin 35 is constrained by the head 26 of plunger 20 which itself is constrained in its movement by the wall of cavity 43. As lever 31 is pivoted from the position shown in FIG. 8 to the position shown in FIG. 9, the lock pin 50 is moved downwardly into the hole in the male member 90 thereby locking the male and female members together. In this position, head 51 of lock pin 50 is now in engagement with flat 36 on the cam surface of cam 30. The thrust of compression spring 53 is insufficient to dislodge the cam 30 from its latched position (FIG. 9). Dislodgement of cam 30 requires a torque force which compression spring 53 is unable to supply.

FIGS. 10-12 depict a more sophisticated latching device having several additional features. In FIGS. 10-12, the plunger 27 has an additional function. In addition to maintaining the edge surface of cam 30 in close contact with the wall of cavity 41, and in addition to confining the movement of the eccentric pin 35 to the projected axis of the plunger, the plunger has a nose portion 28 which is adapted to be received in a recess 101 in a frame member 100. Whether or not nose portion 28 is received in the recess 101 controls whether or not the lock pin 50 may be withdrawn from the latch position shown in FIG. 12.

If the nose portion 28 of plunger 27 abuts against the surface of frame member 100, as illustrated in FIG. 12, withdrawal of lock pin 50 is prevented.

Another feature of the embodiment shown in FIGS. 10-12 is that a slide latch 55 is provided for latching pin 50 in its retracted position. This is illustrated in FIGS. 10 and 11. As seen best in FIG. 11, the forward or left end of the latch slide 55 has an arcuate recess which allows the forward end to be received within an annular groove 52 in lock pin 50. Latch slide 55 is biased to the left by compression spring 59.

When lock pin 50 is latched by latch slide 55 in the retracted position, as illustrated in FIG. 10, removal of the nose 28 of plunger 20 from the recess 101 in frame member 100 is prevented since flat 37 is in abutment against head 51 of lock pin 50 and lever 31 is unable to pivot without moving latched pin 50 upward. The cam 30 is unable to react downward as it attempts to pivot since pin 35 is prevented from moving downwardly by the head 27 of plunger 20 which is confined within the wall of cavity 29.

FIG. 12 illustrates what happens when the male member 105 (FIG. 10) is inserted into the tubular female member 102. When this happens, the forward end of the male member engages slide pin 58 and moves the slide pin 58 and the latch slide 55 to the right, as viewed in FIGS. 10-12. This removes the forward end of the latch slide 55 from the groove 52 of lock pin 50. As a result, the lock pin 50 is no longer prevented from moving upwardly under the thrust of the cam 30 when lever 31 is rotated in a clockwise direction from the position shown in FIG. 10 to the position shown in FIG. 12. When lever 31 is so rotated, lock pin 50 is moved upwardly and the forward end of the lock pin enters hole 106 which is provided in the wall of the male member 105. The male and female members 105 and 102 are now interlocked.

The above described movement of lever 31 and cam 30 is effective to withdraw nose 28 of plunger 20 from the recess 101 in the frame member 100. Thus, the interlocked male and female members are how free to be moved relative to plate 100.

The latch mechanisms of FIGS. 2-5, FIGS. 8-9 and FIGS. 10-12 have been described. While these mechanisms have wide application, they are particularly useful in connection with X-ray apparatus and their usefulness in X-ray equipment will now be described.

Figure 2:
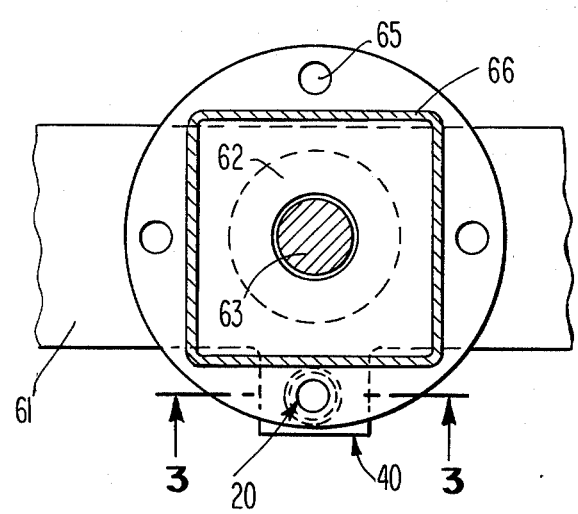
FIG. 2 is a plan view, in section, looking down along the line 2—2 of FIG. 1.
Figure 5:
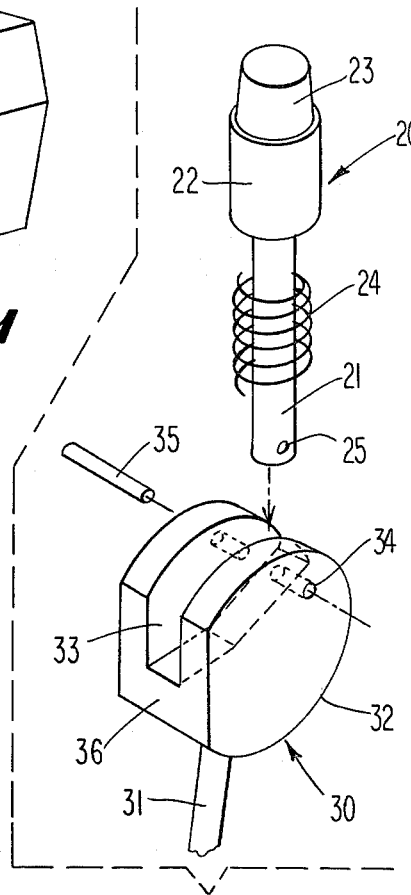
FIG. 5 is an exploded view of the latch plunger and eccentric cam assembly.

The latch mechanism of FIGS. 2-5 is particularly useful in connection with controlling the angular position or orientation of an image amplifier such as is illustrated in FIG. 1 by image amplifier 60. In a typical installation, the image amplifier 60 may be suspended from a vertically-disposed telescoping series of hollow square tubular support members, the lowermost of which is illustrated in FIG. 1 by member 66. Secured to the bottom of the member 66 is a circular disc plate 64 having therein detent holes 65 at various angular positions. In FIGS. 1 and 2, four detent holes 65 are seen spaced 90° apart. Projecting through a center axial hole in plate 64 is a vertical pivot post 63 supported as by flanges 62 for pivotal movement relative to plate 64 and member 66. Supported on the lower of the flanges 62 is a rectangular housing 61 which is connected to and supports the image amplifier 60.

A latch housing 40 containing the latch mechanism of FIGS. 2-5 is secured to the sidewall of the rectangular support member 61. When the latch mechanism is in the position shown in FIG. 3, the nose 23 of the plunger 20 is within one of the detent holes 65 in circular plate 64 thus preventing angular movement of the image amplifier 60 about the vertical axis of the support member 66. When the operator desires to pivot the image amplifier about the vertical axis of member 66, he moves the lever 31 of the latch mechanism from the position shown in FIG. 3 to the position shown in FIG. 4. This retracts the nose 23 of plunger 20 from the detent hole 65. Then, when the nose 23 is out of registry with hole 65, the operator may return the lever partially counterclockwise from the position shown in FIG. 4 toward the position shown in FIG. 3 allowing the nose 23 to abut against the under surface of the circular plate 64. As movement continues, the plunger 20 will come into registry with the next detent hole 65 at which time spring 24 will cause the nose 23 of plunger 20 to enter the detent hole. When plunger 20 is so moved by the action of the compression spring 24, the lever 31 is moved slightly further to the position shown in FIG. 3. During this action, the circular edge 32 of cam 30 rotates on the sidewall of the cavity 45 in housing 40. When the operator senses that plunger 20 has entered the detent 65, he makes sure that the latch mechanism is latched by pushing on the lever 31 in the direction of the position illustrated in FIG. 3.

Figure 6:
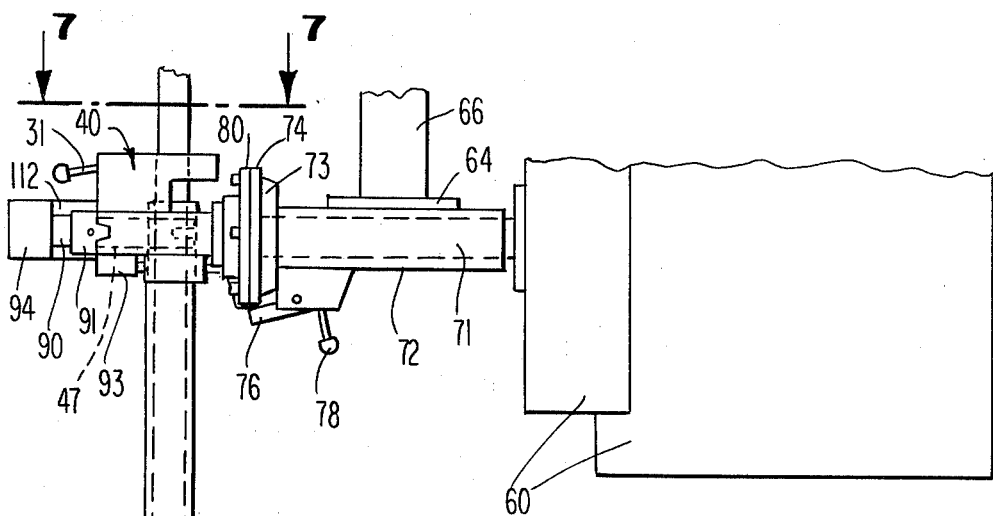
FIG. 6 is an elevational view of a portion of X-ray examination equipment showing the image amplifier and X-ray tube interconnected by mechanical linkage which is latched and unlatched by latch mechanisms provided in accordance with the present invention.
Figure 6:
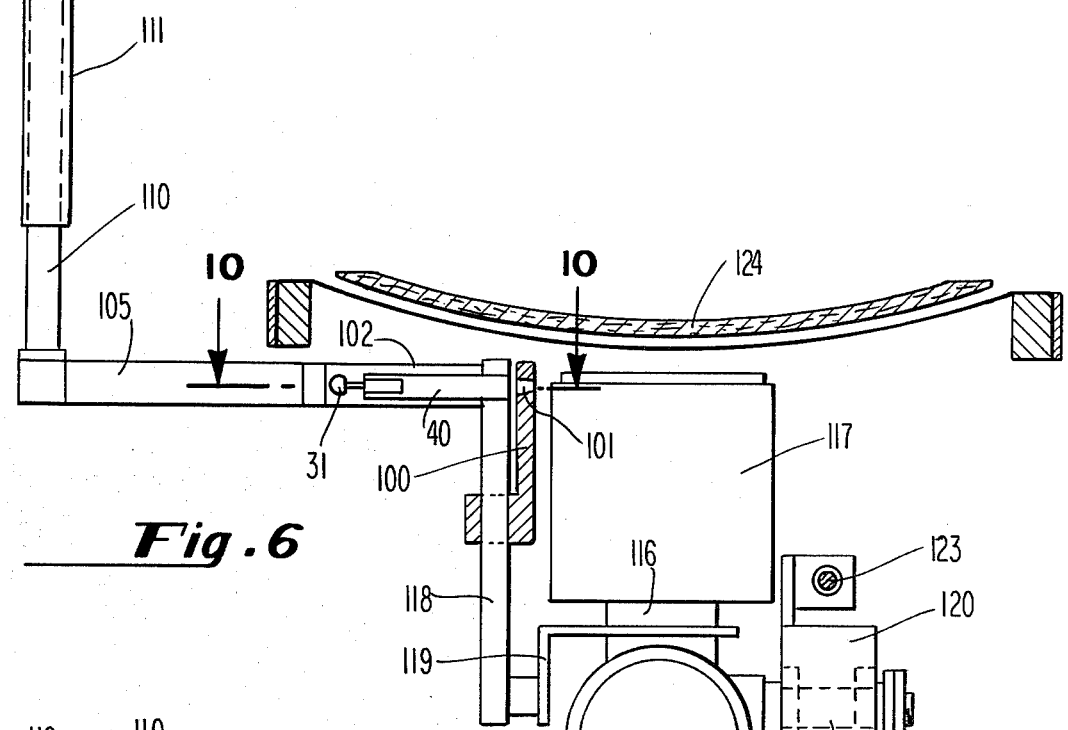
Figure 7:
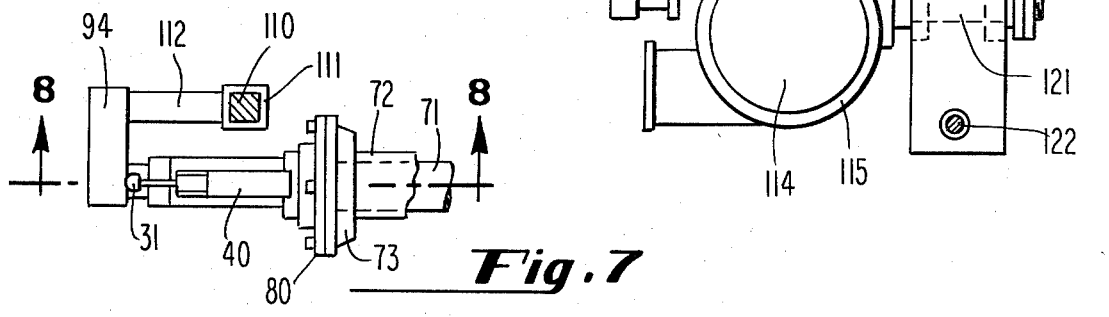
FIG. 7 is a view looking down along the lines 7—7 of FIG. 6.

Utilization in X-ray apparatus of the two forms of latch mechanisms shown in FIGS. 8–9 and in FIGS. 10–12 is illustrated in FIGS. 6–7. In FIG. 6, the image amplifier 60 is shown connected to the X-ray tube 114 by a mechanical linkage which includes the square bar 110 movable vertically within the square tube 111, and the lateral linkage 105 having a shaft which is received within the female tubular member 102. The tubular member 102 is supported at the upper end of a pivotal bar 118 which pivots within a slot of an L-shaped guide member 100. An angle bracket 119 connects the pivotal bar 118 with the X-ray tube support bracket 116. The X-ray tube 114 and its casing 115 are mounted on a short lateral stub shaft 121 which is carried in a trolley 120 which rides on trolley rails 122. A screw 123 having a ball nut dampener is provided. The equipment shown in FIG. 6 is generally similar to that illustrated in FIG. 6 of my co-pending patent application, Ser. No. 865,172, filed Dec. 28, 1977, now U.S. Pat. No. 4,158,777, issued June 19, 1979.

The form of latching mechanism shown in FIGS. 8–9 is useful in connecting the lateral shaft 90 to the tubular member 47. This is illustrated in the upper left portion of FIG. 6 of the present application. The mechanical linkage arrangement in this area is clarified by FIG. 7 which is a view looking down along the line 7—7 of FIG. 6.

The latching mechanism of FIGS. 8–9 used in the upper left portion of FIG. 6 may be referred to as a "quick disconnect" mechanism for it allows the attendant to quickly disconnect the image amplifier 60 from the mechanical linkage which connects the image amplifier to the X-ray tube 114. The capability of quick disconnection is very important. Consider a situation such as this: The attendant has lowered the image amplifier to a position just above and almost in contact with the chest of a patient lying on table top 124. The patient suffers a heart arrest. The doctor wants immediate access to the patient's chest for shock treatment purposes. The X-ray image amplifier is in the way. It must be quickly gotten out of the way. The attendant throws lever 31 from the latched position illustrated in FIG. 9 to the unlatched position illustrated in FIG. 8. This disconnects tubular member 47 from shaft 90, and allows the image amplifier 60 together with the vertical telescoping support member 66, lateral shaft 71, lateral tubular member 72, adapter 80, tubular member 47, latching housing 40 and latch mechanism, to be quickly shoved to one side thereby making the chest region of the patient immediately accessible to the doctor. The mechanical linkage to the X-ray tube is released and unless held by the attendant will tend to fall angularly. However, such fall is restrained by the ball nut damper 123, previously referred to.

In the mechanism illustrated in FIGS. 8 and 9, an adapter plate 80 is used for attaching the body 40 of the latching mechanism to an image amplifier system as may be provided by any one of several different manufacturers. In FIGS. 8 and 9, the shaft 71 which extends from the image amplifier is provided with an end plate 74 having a notch 75 which receives the end of a pivotal latch 76 controlled by a lever 78. Pivotal latch 76 is connected to tubular member 72 which is connected to plate 64 and support 66. The purpose of notch 75 and pivotal latch 76 is to lock the image amplifier by preventing shaft 71 from moving rotationally within tubular member 72 except when latch 76 is released.

The body 40 of the latch mechanism provided by the present invention for latching shaft 90 to tubular member 47 may be provided with means for allowing rotation of shaft 71 within tubular member 72 by disabling latch 76 when shaft 90 is inserted into tubular member 47. As shown in FIGS. 8 and 9, the body 40 of the latch mechanism includes a radial extension having a slot 44 therein which receives a spring loaded plunger 84. Secured to the forward end of plunger 84 is a radial extension 87 having a pin 88 projecting axially therefrom. When plunger 84 is depresses, extension 87 enters a slot 81 in adapter plate 80 and pin 88 enters into the notch 75 to cam latch 76 to open position.

Depression of the spring-loaded plunger 84 is achieved by a radial extension 93 which is welded to the side of the male member 90 and which, when shaft 90 is inserted, enters a slot 46 provided in the body 40. Thus, when the image amplifier 60 is connected to the X-ray tube 114 by the mechanical linkage shown in FIG. 6, the latch 76 is disabled and the image amplifier is free to be moved pivotally on shaft 71.

Referring now to the mechanism shown in FIGS. 10–12 and previously described, this mechanism may be usefully employed in the X-ray apparatus of FIG. 6 to connect the lateral shaft 105 to the tubular member 102 provided that the X-ray tube is vertically oriented as evidenced by the pivotal bar 118 being in a vertical position. If bar 118 is in an angular position relative to the vertical, the plunger 20 will not be in alignment with the recess 101 in the upper end of the L-shaped guide 100, the nose 28 of the plunger 20 will not be able to enter the recess 101, and the end of lock pin 50 will project into the path of shaft 105 and will prevent connection of the shaft 105 to the tubular member 102. This is an important safety feature. It prevents connection and disconnection of the shaft 105 to and from tubular member 102 when the X-ray tube 114 is in any position other than vertical. In any position other than vertical, emission of an X-ray beam could be harmful to persons in the area.

Thus, the latch mechanism of the present invention allows for connection, and for disconnection, of the linkage 102, 105, 110, 111, etc., which connects the X-ray tube 114 to the image amplifier 60 only when the X-ray tube is in such position that the beam is directed vertically upward. For it is only when the nose 28 of the plunger 20 is in alignment with, and enters, hole 101 in guide 100 that the lever 31 may be rotated to the position shown in FIG. 10 wherein the lock pin 50 is withdrawn from the tubular member 102. Also, it is only after the shaft 105 has been inserted into the tubular member 102 to withdraw the slide latch 55 to release the lock pin 50, that the lever 31 can be pivoted from the position shown in FIG. 10 to the position shown in FIG. 12, to interlock the shaft 105 and tubular member 102. In this interlocked position, the nose 28 of plunger 20 is withdrawn from recess 101. If the X-ray tube is now moved to an angular position away from the vertical, disconnection of shaft 105 from tubular member 102 is not possible, since it is not possible to withdraw lock pin 50 from its locked position.

What is claimed is:

1. Latching and indexing means for latching together slidably interfitting first and second members only when said members are in indexed position and for preventing unlatching except when said members are in indexed position, at least one of said members being tubular, said latching and indexing means comprising:
   a. a latch housing secured to the sidewall of said tubular member, said latch housing having first and second cavities interconnected by a channel;
   b. a slot in the sidewall of each of said first and second members for receiving a lock-pin to latch said interfitting members together;
   c. a lock-pin within said first cavity adapted to project through the wall of said housing and through the slot in the sidewall of said tubular member into the slot in the sidewall of said other member to latch said interfitted members together, or into the path of said other member to prevent interfitting of said members;
   d. a spring biasing said lock-pin inwardly toward said first cavity.
   e. a cam within said first cavity, said lock-pin being urged inwardly by said biasing spring into operative engagement with the cam surface;
   f. a lever arm secured to said cam and projecting from said housing and adapted to move said cam pivotally within said first cavity between latched and unlatched positions with respect to said lock-pin;
   g. a plunger within said second cavity having its inward end projecting through said interconnecting channel and connected eccentrically to said cam, said plunger being adapted to be moved by said cam between outward and inward positions;
   h. spring means biasing said plunger toward its outward position;
   i. a fixed frame member having a recess therein for receiving the outward end of said plunger only when said tubular member and latch housing are in indexed position relative to said frame member, the construction being such that when said tubular member is removed from indexed position the outward end of said plunger abuts against the surface of said fixed frame and holds said plunger in its inward position and maintains said cam in its latched position relative to said lock-pin, said cam in said latched position preventing inward movement of said lock-pin, thereby maintaining said lock-pin projecting through the sidewall slot of said tubular member, thereby to block interfitting of said members, or to prevent unlatching of said members if already interfitted.

2. Latching and indexing means according to claim 1 wherein said second cavity has a cross-sectional size and shape similar to that of said plunger, whereby said eccentric connection to said cam is confined to movement only along the projected axis of said plunger, whereby the pivotal axis of said cam is forced to shift during pivotal movement of said cam.

3. Apparatus according to claim 2 wherein, slide latch means are provided for latching said lock pin in retracted position in which said pin does not project into said tubular recess, said lock pin having a circumferential groove in its shank for receiving the end of said slide latch.

4. Apparatus according to claim 3 wherein said slide latch is biased by a biasing spring and has a projection at right angles thereto adapted to receive a force in a direction parallel to that in which said slide latch is movable to move said slide latch against the action of said biasing spring.

* * * * *